US008357168B2

(12) United States Patent  
Wilson et al.

(10) Patent No.: US 8,357,168 B2
(45) Date of Patent: Jan. 22, 2013

(54) MODULAR INJECTION NEEDLE AND SEAL ASSEMBLY

(75) Inventors: Thomas G. Wilson, Guilford, CT (US); Keith Collins, Milford, CT (US); Robert T. Potash, Seymour, CT (US); Andrew Carter, Trumbull, CT (US)

(73) Assignee: Spine Wave, Inc., Shelton, CT (US)

( * ) Notice: Subject to any disclaimer, the term of this patent is extended or adjusted under 35 U.S.C. 154(b) by 415 days.

(21) Appl. No.: 11/850,424

(22) Filed: Sep. 5, 2007

(65) Prior Publication Data

US 2008/0071281 A1    Mar. 20, 2008

Related U.S. Application Data

(60) Provisional application No. 60/843,255, filed on Sep. 8, 2006.

(51) Int. Cl.
  *A61B 17/58* (2006.01)
  *A61B 17/60* (2006.01)
  *A61F 2/00* (2006.01)
(52) U.S. Cl. .................................................... 606/92
(58) Field of Classification Search .............. 606/86 R, 606/90, 92, 94, 246, 279; 623/17.11, 17.12
See application file for complete search history.

(56) References Cited

U.S. PATENT DOCUMENTS

| | | |
|---|---|---|
| 3,750,667 A | 8/1973 | Pshenichny et al. |
| 3,893,445 A | 7/1975 | Hofsess |
| 4,142,517 A | 3/1979 | Stavropoulos et al. |
| 4,313,434 A | 2/1982 | Segal |
| 4,492,576 A | 1/1985 | Dragan |
| 4,545,374 A | 10/1985 | Jacobson |
| 4,609,551 A | 9/1986 | Caplan et al. |
| 4,684,363 A | 8/1987 | Ari et al. |
| 4,736,738 A | 4/1988 | Lipovsek et al. |
| 4,772,287 A | 9/1988 | Ray et al. |
| 4,793,351 A | 12/1988 | Landman et al. |
| 4,904,260 A | 2/1990 | Ray et al. |
| 4,969,888 A | 11/1990 | Scholten et al. |
| 5,108,404 A | 4/1992 | Scholten et al. |
| 5,269,809 A * | 12/1993 | Hayhurst et al. .............. 606/232 |
| 5,300,035 A | 4/1994 | Clement |
| 5,318,524 A | 6/1994 | Morse et al. |
| 5,331,975 A | 7/1994 | Bonutti |
| 5,411,491 A | 5/1995 | Goldhardt et al. |
| 5,431,676 A | 7/1995 | Dubrul et al. |
| 5,454,365 A | 10/1995 | Bonutti |
| 5,505,732 A | 4/1996 | Michelson |
| 5,514,153 A | 5/1996 | Bonutti |
| 5,549,565 A | 8/1996 | Ryan et al. |
| 5,556,429 A | 9/1996 | Felt |
| 5,562,736 A | 10/1996 | Ray et al. |
| 5,571,181 A * | 11/1996 | Li .............................. 623/23.75 |
| 5,645,597 A | 7/1997 | Krapiva |

(Continued)

*Primary Examiner* — Sameh Boles
(74) *Attorney, Agent, or Firm* — Hoffmann & Baron, LLP

(57) ABSTRACT

A kit for injecting a biomaterial into an intradiscal space accessed through an opening in the disc annulus comprises a plurality of needles, each sized for introduction through the annulus opening with a passageway for injecting the biomaterial therethrough, and each including a distal end to be disposed within the intradiscal space when the needle extends through the annulus opening. Each needle includes a stop affixed thereto at different pre-determined distances from the distal end to define the location of the distal end within the intradiscal space when the needle extends through the opening in the annulus. The kit further includes a plurality of seals defining a bore for sliding engagement with a needle, each of the plurality of seals including a sealing face for engaging the annulus around the needle. Each sealing face defines a differently configured area of contact, such as circular, elliptical, tapered and threaded.

8 Claims, 18 Drawing Sheets

U.S. PATENT DOCUMENTS

| | | |
|---|---|---|
| 5,667,520 A | 9/1997 | Bonutti |
| 5,681,289 A | 10/1997 | Wilcox et al. |
| 5,685,826 A | 11/1997 | Bonutti |
| 5,697,889 A | 12/1997 | Slotman et al. |
| 5,702,446 A | 12/1997 | Schenck et al. |
| 5,716,416 A | 2/1998 | Lin |
| 5,720,726 A | 2/1998 | Marcadis et al. |
| 5,752,969 A | 5/1998 | Cunci et al. |
| 5,762,629 A | 6/1998 | Kambin |
| 5,827,318 A | 10/1998 | Bonutti |
| 5,860,997 A | 1/1999 | Bonutti |
| 5,906,577 A * | 5/1999 | Beane et al. ............... 600/207 |
| 5,954,739 A | 9/1999 | Bonutti |
| 5,968,062 A | 10/1999 | Thomas et al. |
| 6,017,305 A | 1/2000 | Bonutti |
| 6,017,350 A | 1/2000 | Long |
| 6,018,094 A | 1/2000 | Fox |
| 6,039,761 A | 3/2000 | Li et al. |
| 6,042,596 A | 3/2000 | Bonutti |
| 6,048,346 A | 4/2000 | Reiley et al. |
| 6,083,202 A | 7/2000 | Smith |
| 6,086,595 A | 7/2000 | Yonemura et al. |
| 6,135,999 A | 10/2000 | Fanton et al. |
| 6,174,311 B1 | 1/2001 | Branch et al. |
| 6,187,023 B1 | 2/2001 | Bonutti |
| 6,210,397 B1 | 4/2001 | Aboul-Hosn et al. |
| 6,258,872 B1 | 7/2001 | Stedronsky |
| 6,370,420 B1 | 4/2002 | Kraft |
| 6,371,990 B1 | 4/2002 | Ferree |
| 6,436,143 B1 | 8/2002 | Ross et al. |
| 6,558,390 B2 | 5/2003 | Cragg |
| 6,579,291 B1 | 6/2003 | Keith et al. |
| 6,620,162 B2 * | 9/2003 | Kuslich et al. ............... 606/53 |
| 6,716,216 B1 * | 4/2004 | Boucher et al. ............. 606/86 R |
| 6,726,691 B2 | 4/2004 | Osorio et al. |
| 6,805,695 B2 | 10/2004 | Keith et al. |
| 6,814,736 B2 | 11/2004 | Reiley et al. |
| 6,981,981 B2 | 1/2006 | Reiley et al. |
| 7,004,945 B2 | 2/2006 | Boyd et al. |
| 2001/0021852 A1 | 9/2001 | Chappius |
| 2002/0147497 A1 | 10/2002 | Belef et al. |
| 2003/0009227 A1 | 1/2003 | Lambrecht et al. |
| 2003/0082169 A1 | 5/2003 | Boyd |
| 2003/0083642 A1 | 5/2003 | Boyd et al. |
| 2004/0059339 A1 | 3/2004 | Roehm, III et al. |
| 2004/0068268 A1 * | 4/2004 | Boyd et al. .................... 606/92 |
| 2004/0073213 A1 | 4/2004 | Serhan et al. |
| 2004/0098017 A1 | 5/2004 | Saab et al. |
| 2004/0186471 A1 | 9/2004 | Trieu |
| 2004/0229878 A1 | 11/2004 | DiMauro et al. |
| 2005/0070913 A1 | 3/2005 | Milbocker et al. |
| 2005/0102030 A1 | 5/2005 | Yuksel et al. |
| 2005/0209602 A1 * | 9/2005 | Bowman et al. ................ 606/90 |
| 2005/0234425 A1 | 10/2005 | Miller et al. |
| 2006/0004458 A1 * | 1/2006 | Collins et al. .............. 623/17.16 |
| 2007/0043374 A1 * | 2/2007 | Evans ............................ 606/86 |

* cited by examiner (a)       (b)       (c)

(d)       (e)       (f)

(g)

(a)

(b)

(a)

(b)

(c)

(a)

(b)

(a)

(b)

(a)

(b)

MODULAR INJECTION NEEDLE AND SEAL ASSEMBLY

RELATED APPLICATIONS

This application claims priority to provisional application No. 60/843,255, filed on Sep. 8, 2006, the disclosure of which is incorporated herein by reference. This application relates to co-pending applications Ser. Nos. 11/170,010; 11/170,577; 11/170,382; 11/169,405; 11/170,588 and 11/170,657, all filed on Jun. 29, 2005, and all of which claim priority to provisional application No. 60/683,665, filed on Jun. 29, 2004. The disclosure of each of these co-pending applications is incorporated herein by reference.

BACKGROUND

The present invention relates to systems and methods for the treatment of the spine, and especially the interbody disc space. More specifically, the invention concerns the injection of a biomaterial into a spinal space, such as the intradiscal space.

Spine fusion procedures represent the state of the art treatment for intervertebral disc problems, which generally involve open surgery and the use of interbody fusion cages and spinal fixation systems to stabilize the fusion site. An alternative treatment under evaluation is to replace or augment the disc or nucleus pulposus with a prosthetic device. Examples of some devices currently under investigation include in-situ cured polymers such as polyurethanes and protein polymers, which may have properties varying from a rubbery hydrogel to a rigid plastic. Problems associated with these devices occur during insertion, whereby the pressure required to fill the disc space can cause leakage of the material into sensitive adjacent areas.

A number of devices are available for distracting vertebral bodies or for injecting material into the disc. Some devices are capable of both distraction and injection using the same instrument. These types of devices use a deflated balloon attached to a cannula and inserted between the vertebral bodies. The balloon is inflated with a prosthetic fluid through the cannula to distract the vertebral bodies. This requires high-pressure delivery of the fluid to achieve the pressure needed to distract the vertebral bodies and the balloon and fluid permanently remain in the disc space. Alternatively, a separate device is used to inject the prosthetic fluid around the balloon and the balloon is used strictly for distraction after which it is deflated and removed.

Much of the prior art devices and methods contemplate free injection of biomaterial into a spinal space which may lead to uncontrolled leakage. The art also describes injection of the material into a deflated balloon, which requires leaving the balloon inside the disc space. Lastly, some methods require insertion under high pressure, thereby creating a potential for the prosthetic fluid to ooze or seep out of the disc space intra-operatively.

There is therefore a need for a system and method for introducing a biomaterial into a spinal space that is not prone to the problems of the prior art, especially the leakage problem experienced by the high pressure injection systems. This need extends to systems that can be easily utilized in a minimally invasive procedure.

SUMMARY OF THE INVENTION

The present invention contemplates a modular injection needle assembly. The assembly includes an injection needle which includes an injection cannula for introduction of a fluent biomaterial, such as an injectable nucleus material, into a disc space. The injection needle may also include a vent cannula for venting fluid from the disc space as it is being filled with the biomaterial.

The injection needle is provided with a stop that is integral with or fastened to the needle. The stop may be positioned at different distances from the distal end of the needle. In one embodiment of the invention, a kit is provided with a selection of injection needles with stops at these different distances.

A mountable and removable seal is also provided with the injection needle assembly. The seal is configured to seat against the stop and maintain its position until removed after the procedure is complete. The invention contemplates a variety of seal configurations from which the surgeon may select a configuration that is optimum for the particular surgical procedure and disc anatomy. The variety of seal configurations includes cylindrical and elliptical seals and cup-shaped seals that are configured for fluid-tight contact with the outer surface of the annulus. The variety of seals also includes conical seals that are configured to be pressed into an opening in the annulus. In a further alternative, the seals may include self-anchoring features, such as external threads on the conical seals.

The variety of seals may be provided in a kit, along with the selection of injection needles. Thus, the surgeon may create an injection needle assembly that is optimized for the patient and the procedure.

DESCRIPTION OF THE PREFERRED EMBODIMENTS

Figure 1:
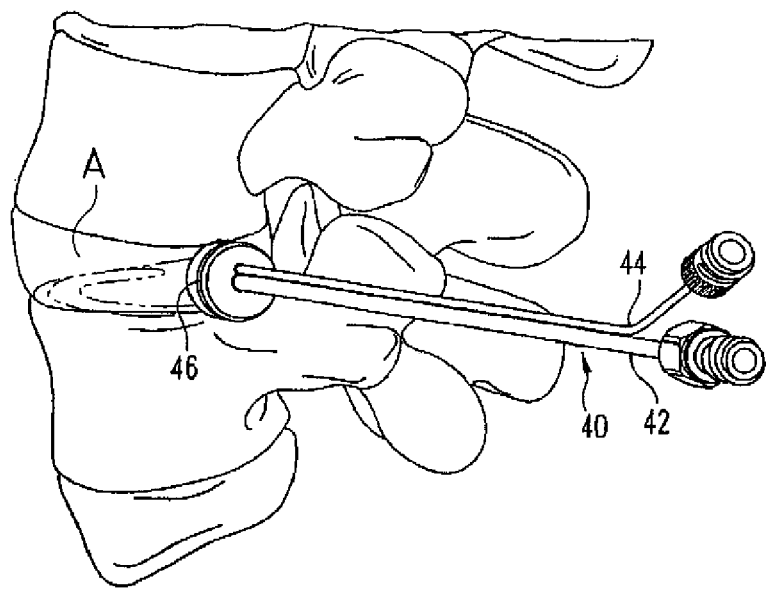
FIG. 1 is an enlarged pictorial view of a vented injection needle for introduction of curable biomaterial into a disc space.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

In a particular procedure that may incorporate the present invention, an injectable nucleus is surgically introduced into the spine as a replacement for or augment to the natural nucleus pulposus. The injectable nucleus is preferably a curable biocompatible polymer with properties that emulate those of the natural human disc. A suitable injectable nucleus material is disclosed in U.S. Pat. Nos. 6,423,333; 6,033,654; and 5,817,303, which issued to Protein Polymer Technologies, Inc. The disclosures of these patents are incorporated herein by reference. These patents disclose a proteinaceous curable polymer that has physical properties close to those of the human disc nucleus pulposus and that includes certain adhesive properties that allow the polymer to adhere to the disc annulus and any remaining disc nucleus pulposus.

In a first step of the technique, the constituents of the injectable nucleus material are prepared in a mixing system, such as the mixing system disclosed in co-pending, commonly assigned patent application Ser. No. 10/803,214, entitled "Systems and Methods for Mixing Fluids", the disclosure of which is incorporated herein by reference. The mixing system is placed on the sterile table until it is needed for the mixing and injection step.

Where the biomaterial is an injectable nucleus, access to the intradiscal space is required. While many surgical approaches may be used, in one specific embodiment, the surgeon will use an extraforaminal mini-open approach to the disc. This may be either by a lateral retroperitoneal approach or a paramedian approach through the paraspinal muscles of the back. Access to the nucleus is gained through an extraforaminal annulotomy, so as to not expose the spinal canal or foramen to any undue risk. The annulus is identified and a minimal annulotomy is performed to gain access to the intradiscal space. The nucleus pulposus is then partially or completely removed using known techniques, such as using pituitary rongeurs and/or curettes. The nucleotomy should be fully irrigated once all loose fragments have been manually removed.

Once a predetermined amount of disc nucleus is removed, the size of the space may be verified, such as by visualization and/or use of a saline injected balloon. When the disc space is ready to receive the injectable nucleus, the disc space may be distracted using several techniques. In one technique, distraction of the disc is accomplished using a non-compliant inflatable spherical balloon, such as a 15 mm diameter spherical balloon.

Once the desired amount of distraction has been obtained, the distraction tool, such as the spherical balloon, may be removed from the disc. At this point, a trial balloon may be used again to estimate the volume of injectable nucleus needed to the fill the distracted space.

With the disc space maintained in distraction (whether by physical positioning of the patient or by external instrumentation), the injectable nucleus composition may be mixed and injected into the disc space. Thus, an injection needle may be provided as part of an injection assembly 40, as shown in FIG. 1. Details of the injection assembly 40 may be gleaned from previously incorporated co-pending application Ser. No. 11/170,010, and particularly the description associated with FIGS. 13-16 thereof, the disclosure of which is incorporated herein by reference. The injection needle 42 extends through a seal element 46 that is configured to provide an essentially fluid tight seal against the disc annulus A. A vent 44 also extends through the seal 46. The seal 46 is shown in more detail in FIG. 2. In a particular form of the construction, the seal 46 includes a body 48 that is preferably formed of a resilient material that can be compressed slightly under manual pressure to conform to the irregular external surface of the disc. The body 48 defines a sealing face 50 that bears against the disc annulus A (FIG. 1) to create a fluid tight seal.

Figure 2:
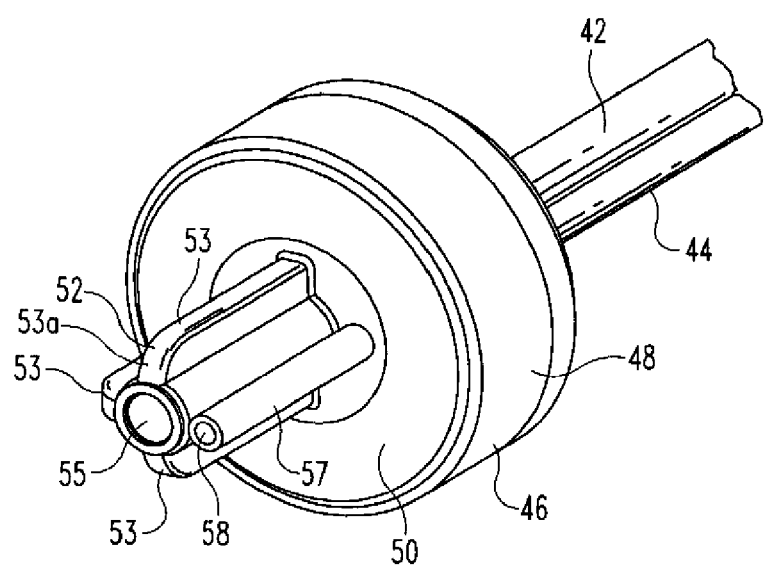
FIG. 2 is a front perspective enlarged view of the vented injection needle shown in FIG. 1.

Extending from the sealing face 50 is an engagement boss 52. The boss 52 is preferably configured in accordance with the shape of the annulotomy cut into the annulus. As illustrated in FIG. 2, the boss 52 is also cruciate in shape with wings 53 that are sized to fit within corresponding legs of a cruciate cut into the annulus A. The leading edges 53a of the wings 53 can be rounded to facilitate placement of the boss 52 within the annulotomy.

The vent 44 provides an additional wing 57 for the boss 52. The wing 57 includes a channel 58 that integrates with the hollow vent 44. Preferably, the vent wing 57 is co-extensive with the other wings of the boss 52. Alternatively, the working end of the wing 57 can project slightly farther into the disc space. The injection needle 42 feeds to a channel 55 defined in the boss 52 to provide a pathway for the injectable nucleus into the disc cavity.

In accordance with another aspect of the procedure, the needle is introduced through the annulotomy, while carefully retracting the nerve root, until the seal 46 seats against the annulus. Preferably, the needle is positioned so that the vent 44 is facing upward during the injection, as depicted in FIG. 1. Pressure is applied to the seal 46 to ensure that no injectable nucleus leaks out between the seal and annulus. Preferably, this pressure is applied manually by the surgeon by simply pressing the injection catheter 42 toward the annulus. Since the injectable nucleus injection occurs at low pressures, the amount of force required to maintain a fluid-tight seal between the seal face 50 and the annulus is minimal.

The injectable nucleus is injected into the space until injectable nucleus is seen flowing through or out of the vent tube. At this point, the injection is stopped and the needle is held in place until the injectable nucleus takes its initial set. A microscope or loupe may be used to visualize the injection process. The injectable nucleus composition is preferably allowed to substantially completely cure before the injection needle assembly 40 is removed and the surgical site is closed. The cure period depends upon the particular injectable nucleus material. For the specific proteinaceous polymer discussed above, the cure period is a minimum of about five minutes.

The seal 46 is formed of a resilient and deformable material so that it can be compressed against the annulus A to form a fluid tight seal. In a particular form, the seal 46 is formed of SILASTIC® or a similar elastomeric material. The seal 46 in the illustrated embodiment is cylindrical with a circular sealing face 50; however, other configurations are contemplated provided they can adequately conform to the outer surface of the disc annulus.

The procedures described heretofore are particularly well suited for open surgical procedures where a microdiscectomy is performed to remove all or a portion of the disc nucleus. One such procedure is for the treatment of degenerative disc disease (DDD) where a total or partial nucleotomy is indicated. In such an open procedure access to the spinal disc is accomplished through an incision made through the skin and subcutaneous body tissue down to the surgical site is displaced and retracted. In the case of DDD, the annulus is typically relatively intact so that a minimal annulotomy is required to gain access to the intradiscal space. It is preferred that the opening is as small as feasible to minimize damage to the annulus. In one embodiment, access can be via a K-wire over which a dilator, or a series of dilators, is passed. However, the nucleus pulposus may be significantly under-hydrated or may contain fissures throughout the nucleus material, producing patient pain and giving rise to the need for a total or substantially total discectomy.

In such a DDD procedure, in addition to the steps described hereinabove, the surgeon may also chose to perform an intraoperative step of determining the integrity of the annulus, to confirm that the annulus is competent to withstand the distraction and injectable nucleus injection pressures. To accomplish this test, upon completion of the partial or total nucleotomy and creation of an intradiscal space within the disc annulus, a saline solution may be injected into the intradiscal space through the annulotomy opening. A saline solution is preferred since it is relatively easy to aspirate for removal from the intradiscal space. However, other suitable solutions may also be used. The saline solution may be injected through a vented needle, in design and construction similar to the needle 40 shown in FIGS. 1-2. When the saline injection is under relatively low pressure (on the order of 25-40 psi under thumb pressure from the syringe and pressing the seal 46 against the external surface of the annulus), this step evaluates the integrity of the disc annulus—i.e., detects whether fissures or rents may be present in the annulus. This detection may be by tactile feel and/or by observation of leakage only at the injection needle site.

Alternatively, or additionally, the injected saline solution may be used to determine the volume of the disc space to be filled with injectable nucleus material. If preferred, a trial balloon may be used to ascertain the volume of the intradiscal space to be filled. After the annulus integrity and volume tests have been completed, suction is applied to aspirate the nuclear cavity and a surgical swab may be used to wick away excess moisture that may interfere with the injection of the injectable nucleus material. Thereafter, the surgeon may use a distraction balloon to apply a distraction force within the intradiscal space to distract the opposing vertebral bodies on either side of the intradiscal space, further separating apart such vertebral bodies. A subsequent saline test may be conducted to further verify the integrity of the annulus. The injectable nucleus may then be sealably injected under pressure using the vented needle 40 as described hereinabove. Such injection of injectable nucleus is preferred to be at a pressure that is not greater than the pressure under which the saline solution is injected and is typically on the order of 25-40 psi. While the saline solution has been described as preferably being injected with a vented needle such as described herein, it should be appreciated that a needle without a vent, but with a sealing element, could also be used in the practice of the annulus integrity test.

Other open surgical procedures are also contemplated, such as an adjunct to microdiscectomy (AMD) procedure. An AMD procedure is indicated where a total discectomy is not required, or more particularly where only a partial discectomy is necessary to restore normal or near normal function to the affected disc. In a typical case, the affected disc has a herniation or tear in the disc annulus. Access to the intradiscal space is thus available through the tear in the annulus.

Prior to the start of the surgery, the injectable curable polymer constituents are pre-loaded into the mixing assembly, as described above, and left on the sterile instrument table until the appropriate time for injection of the injectable nucleus material. The surgeon uses a traditional open or microdiscectomy technique of preference for access to the disc herniation site. Typically, the patient will be placed on a laminectomy frame in the prone position with the spine flexed to aid intraoperative exposure. The ligamentum flavum and laminar edge are identified. A hemilaminectomy/medial facetectomy may be performed as necessary, with the aid of lateral fluoroscopy. Exposure of the hernia proceeds in a known manner, taking care to protect the dura and nerve root. The epidural space is explored to ensure that all disc fragments have been identified.

Once the disc herniation has been identified, a determination is made as to whether a further annulotomy is needed for improved access. If so, an annulotomy may be performed as described above. The herniated disc tissue is then removed according to known techniques, such as using pituitary rongeurs and/or curettes. Laminar distraction and/or flexion of the hips can be used to aid in exposure of the hernia site. In addition, distraction of the affected disc may be desired to improve the stability of the disc. This distraction may be accomplished using any of the techniques described above. If sufficient disc tissue has been removed around the herniation site, a distraction balloon may be used, provided that the balloon is removed once the desired distraction has been achieved.

The balloon distraction may also be supplemented in a two stage distraction technique described as follows. After a total or partial nucleotomy has been performed, in the first stage, a distraction balloon is inserted into the intradiscal space. The balloon is then inflated to gain distraction of the anterior column of the disc space.

In the second stage, a secondary distraction instrument is introduced to act on any posterior bony structures at the particular intervertebral level in accordance with known surgical techniques. The secondary instrument is used to obtain distraction of the posterior column at an appropriate amount decided by the surgeon. The nature and amount of this second stage distraction may increase the overall amount of distraction of the total space, change the lordotic angle at the intervertebral level or cause no appreciable increase in the overall distraction of the space.

Once the appropriate amount and type of secondary distraction has been obtained, the first stage distraction balloon is removed, while the secondary instrument remains in place to prevent any loss of distraction that may occur. With the distraction balloon removed, the injectable nucleus may be injected as described above. After suitable distraction has been achieved, a saline solution as described above with respect to the DDD procedure may be injected through a vented needle into the intradiscal space to check the integrity of the annulus and to determine that there are no other leakage paths, as well as to estimate the volume of the intradiscal space to be filled. While this annulus integrity test is described as being conducted after distraction, it may also be done after removal of nucleus and prior to distraction.

When the nuclear cavity has been prepared, the surgeon mixes the injectable nucleus constituents, as described above, to prepare the injectable nucleus material for injection. An injection needle (which is not required to be a vented and sealed needle) is introduced through the opening in the annulus until the needle tip reaches the far side of the cavity. As the injectable nucleus material is injected, the needle is preferably angled side-to-side and gradually withdrawn toward the annulus to ensure a complete fill of the space. When the injectable nucleus material is detected at the inner border of the annulus opening, the injection is stopped and the needle is removed from the site. Alternatively, a vented needle 40 with a seal 46 may be used, such as where the rent through the annulus is relatively small and not too irregular. With a vented needle 40, the injection is stopped when the injectable nucleus material is seen at the vent. It is contemplated that the injectable nucleus material will be injected under pressure, typically on the order of 25-40 psi, to ensure complete fill of the cavity, with the seal 46 of the vented needle 40 being pressed against the annulus during injectable nucleus injection.

Another procedure for percutaneous direct injection of a curable biomaterial for treatment of degenerative disc disease is indicated where the disc annulus is generally intact, but the nucleus pulposus has been compromised, either by dehydration or the creation of fissures and the patient suffers from significant pain. In some DDD procedures, for example, as described hereinabove, some or all of the nucleus is removed to create an intradiscal space for injection of curable biomaterial. The defective or degenerated nucleus is not removed, but is instead augmented by a curable biomaterial or injectable nucleus material in a percutaneous procedure.

In a percutaneous procedure, access to the spinal disc is achieved simply by introduction of a relatively small and sharp cannulated device, which may include a needle, through the skin and body tissue down to the surgical site under fluoroscopy or by using other conventional surgical navigation techniques. No incision is made nor is any body tissue retracted. Further, injection is continued by insertion of the cannulated device through the annulus into the nucleus pulposus, preferably without additional dilators and without removing any of the annulus tissue. As such, a percutaneous procedure provides a minimally invasive approach to treating DDD conditions.

Figure 3:
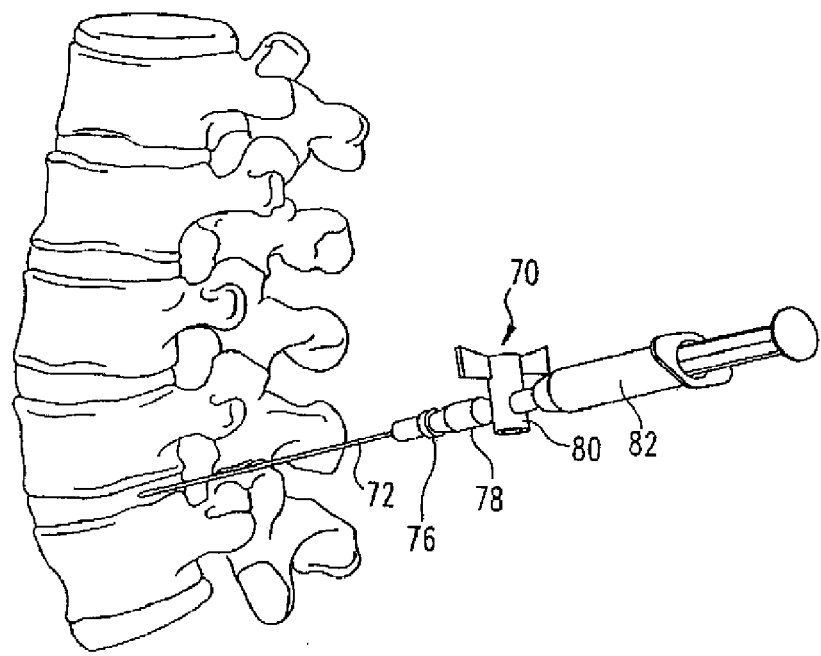
FIG. 3 is a lateral pictorial view of the spine with an injection assembly positioned to introduce a curable biomaterial into an affected disc in a percutaneous procedure.
Figure 4:
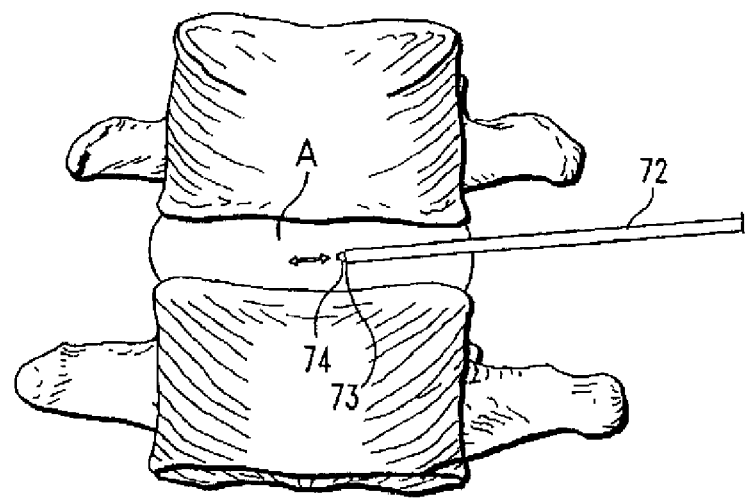
FIG. 4 is an enlarged view of the disc shown in FIG. 3 with the injection needle and docking cannula of the injection assembly positioned within the disc annulus.
Figure 19:
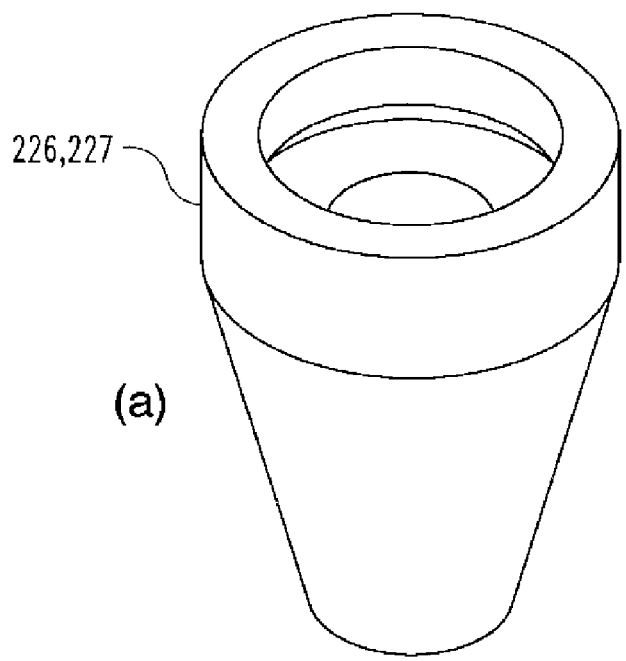
FIGS. 19(a)-19(b) are perspective and cross-sectional views of the seal body of a conical seal for use with the needle assembly shown in FIG. 9.
Figure 19:
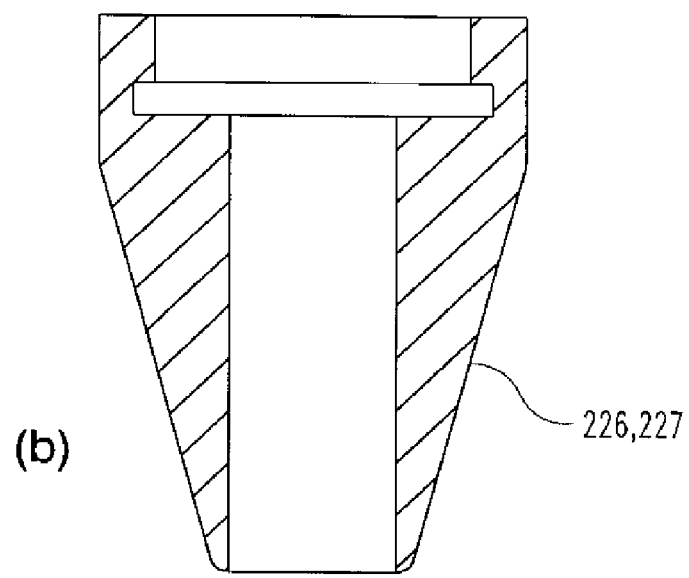

In accordance with the percutaneous procedure, the injectable nucleus material is prepared in the same manner described above, with the loaded mixing assembly and crosslinker syringes made available on a sterile instrument table until the appropriate time for injection of the injectable nucleus material. In particular, an injection assembly 70 shown in FIG. 3 may be used to accomplish the injection step. Details of the injection assembly may be obtained from previously incorporated co-pending application Ser. No. 11/170, 657 with particular attention to FIGS. 19-20 thereof, the disclosure of which is incorporated herein by reference. The assembly 70 includes a sharp cannulated device, such as a thin-walled docking cannula 72 with an integral mating hub 76. In this particular construction, the cannula 72 has a relatively smooth outer surface and substantially constant outer and inner diameters along its length. An injection needle 74 (FIG. 4) is slidably disposed within the docking cannula in a relatively close dimensional fit. The needle 74 is integral with a hub 78 that may be configured to mate with the hub 76 of the cannula. A stopcock valve 80 is fluidly connected to the hub 78, and the injection syringe 82 is configured to engage the stopcock valve in any known manner effective to create a fluid tight connection.

The patient is preferably placed in a prone position on an appropriate conventional Andrews frame or equivalent table, in the proper lordotic posture with the hips flexed to aid in the exposure of the posterior disc. The docking cannula 72 is introduced to the disc in an extraforaminal location using a typical posterolateral discography approach. A guide stylet may extend through and be disposed in the cannula to assist in passing the cannula through the body tissue to the disc annulus A. Once the docking cannula is properly docked within the annulus, it forms a substantially fluid-tight interface with the disc annulus. Since the procedure does not require an annulotomy, the elasticity of the annulus and other tissues surrounding the disc cause those tissues to compress around the cannula 72 to create a seal. Once the cannula 72 has been docked within the annular wall the injectable nucleus may be prepared and injected under pressure into the nucleus pulposus to fill all voids, interstices and fissures that may exist in the existing nucleus. When the polymer cures in situ, it adheres to the existing natural disc material for essentially seamless integration with the existing disc nucleus, thereby substantially restoring the normal disc function.

Once the desired amount of injectable nucleus material has been injected, the stopcock valve 80 is closed to maintain the fluid pressure. The injection assembly 70 is preferably held in place during the minimum cure time, which is about five minutes in the specific embodiment. After the initial cure period, the injection needle is removed. The natural disc and augmenting injectable nucleus material will collapse to fill the minimal channel left by removal of the injection needle 74.

While the injection assembly 70 has been described herein as including the docking cannula 72 and a separate injection needle 74, it should be understood that other injection alternatives are contemplated. For example, in certain situations where perhaps the surgeon has more time to inject a curable material than the particular embodiments described, the needle 74 itself may be directly injected without use of the docking cannula 72.

Figure 5:
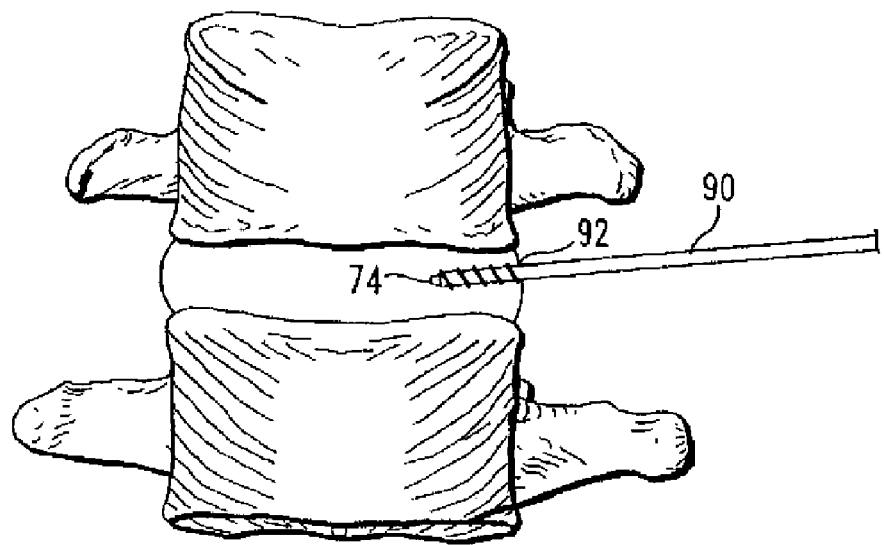
FIG. 5 is an enlarged view of a disc with a docking cannula according to a further embodiment with the injection needle extending therethrough into the disc space.
Figure 6:
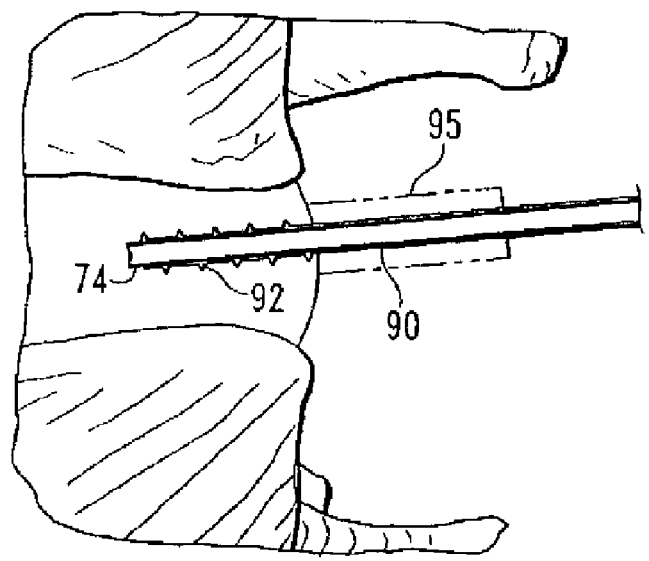
FIG. 6 is an enlarged cross-sectional view of the docking cannula and injection needle depicted in FIG. 5.

In an alternative approach depicted in FIGS. 5-6, a docking cannula 90 may be provided that includes a threaded tip 92. The threads are configured to pierce the annulus as the docking cannula 90 is rotated. With this alternative, the hub may be modified from the hub 76 of the cannula 72 to provide a gripping surface suitable for manual threading of the cannula 90 into the disc annulus. Thus, the threaded cannula 90 may provide a more positive anchoring of the cannula 90 to the annulus. In addition, a seal may be provided between the threaded tip 92 and the wall of the annulus since the cannula 90 is threaded into the annulus without an annulotomy being performed. As such, it is considered that such a threaded cannula 90 would allow injection of curable biomaterial at pressures greater than 160 psi and potentially up to as high as 200 psi.

In a modification of the threaded docking cannula 90, a flange 95 may be defined on the cannula, as depicted in phantom lines in FIG. 6. This flange 95 may act as a stop to control the amount of insertion of the threaded tip 92 into the disc annulus. The flange may also assist in providing and maintaining a fluid-tight seal at the opening formed in the annulus. The flange may also include a fitting, such as a Luer lock fitting, to mate with the hub 78 of the injection needle. In this case, the fitting is preferably sized so that the fitting is accessible outside the percutaneous wound in the patient. Such a flanged cannula may have particular application in the open DDD and/or AMD surgical procedures described hereinabove.

Figure 7:
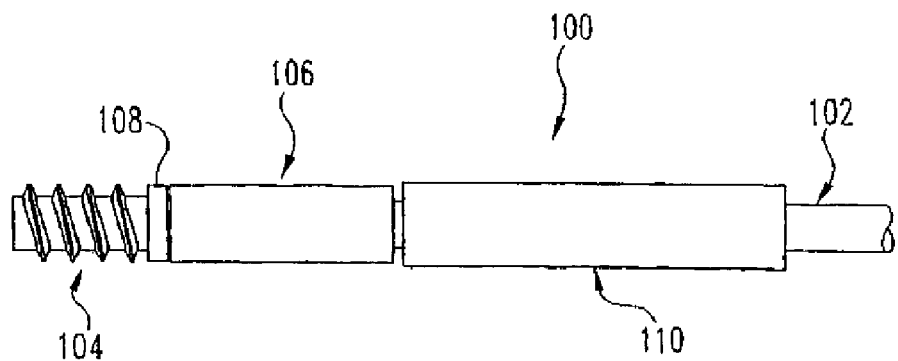
FIG. 7 is an enlarged view of a disc with a docking cannula according to a further embodiment with the injection needle extending therethrough into the disc space.
Figure 8:
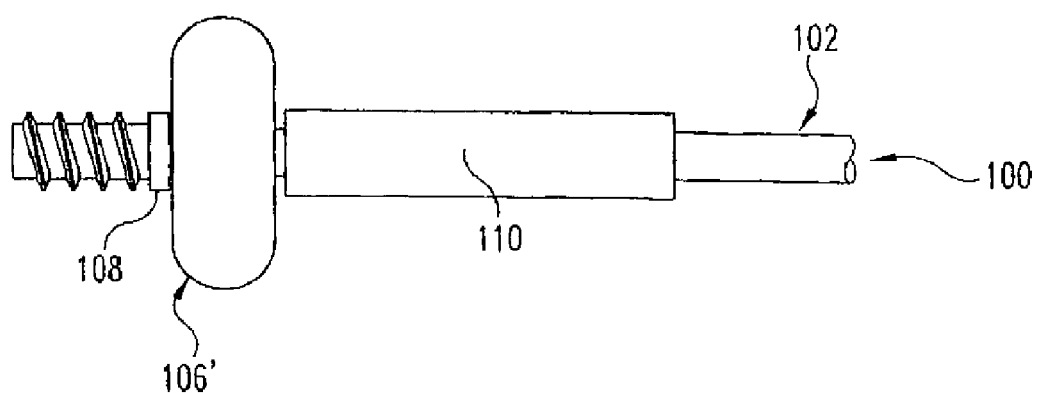
FIG. 8 is an enlarged cross-sectional view of the docking cannula and injection needle depicted in FIG. 7.

In a further modification, a threaded docking cannula 100, depicted in FIGS. 7-8, includes an expandable flange 106. The cannula includes a cannula body 102 terminating in threads 104 for engagement within the disc annulus, as with the embodiments described above. The expandable flange 106 is interposed between a fixed collar 108 and a sleeve 110 that is slidably disposed about the cannula body 102. The expandable flange is configured to have an un-expanded condition 106, as shown in FIG. 7 and then to move to an expanded condition 106', shown in FIG. 8, upon pressure from the sleeve 110. In a specific embodiment, the flange 106 is formed of a resilient material that deforms when pressed by the sleeve but returns substantially to its un-expanded condition (FIG. 7) when the pressure is removed. In its un-expanded condition, the flange 106 has a small enough outer profile or diameter to be used percutaneously.

In the previous embodiments, the sealing element of the injectable nucleus injection device is fixed relative to the injection tube or cannula. These devices are therefore limited to a particular needle length. Variations in needle length may allow a surgeon to introduce the injectable nucleus at a desired location within the disc. Moreover, different needle lengths may be necessary to account for variations in patient anatomy. Similarly, the devices described above include a certain seal geometry. However, in some procedures, the anatomy of the disc, and particularly the disc annulus, may require a more specialized seal configuration to effectively seal around the disc access opening. For instance, in an open DDD procedure, an annulotomy is used to form a controlled access opening in the annulus. On the other hand, in an AMD procedure, access to the disc nucleus may be through an irregular opening in the annulus that may be the result of a tear or rupture. The injection seal that is suitable for the DDD procedure may not be sufficient for the AMD procedure. Other variations in disc anatomy may dictate or restrict the geometry of the seal that is acceptable.

Thus, the present invention contemplates a modular injection needle and seal apparatus. In particular, a modular injection apparatus 200 shown in FIG. 9(*g*) includes an injection needle 210 with a modular seal 220 mounted thereon. The needle 210 may be configured like the needle 40 described above, namely including a primary cannula 212 through which the injectable nucleus may be injected and a secondary vent cannula 214. As shown in FIGS. 10(*a*)-(*b*), the primary cannula may terminate in a fitting 213 for engagement to a source of injectable nucleus fluent material. Similarly, the vent cannula 214 may also terminate in a fitting 215 for engagement to a reservoir for receiving fluid venting through the cannula. It should be understood, however, that in some applications the injection needle 210 may be used only with a primary cannula 212 without the vent cannula 214.

As further shown in FIGS. 10(*a*)-(*b*), the injection needle 210 includes a stop 217 connected to the needle offset from the distal end 211 of the needle. The stop 217 is positioned at a distance L (FIG. 9(*g*)) from the distal end. This distance varies among a selection of injection needles 210 from a base location (0 mm) to a farthest upstream position (15 mm in the illustrated example). The selection of injection needles may have the stop 217 located at 5 mm increments from this base location. Thus, in the illustrated example, the selection of injection needles 210 will have the stop 217 located at 0 mm, 5 mm, 10 mm and 15 mm. The base location (0 mm) is preferably established so that the distal end 211 extends just inside the interior surface of the disc annulus A (FIG. 1) when the seal 220 is engaged to the outer surface of the annulus. The base location is preferably indexed to a minimum expected thickness for the disc annulus. The alternative stop positions may thus account for variations in annulus geometry or may position the distal end 211 at variable incursions into the interior of the disc space.

Figure 11:
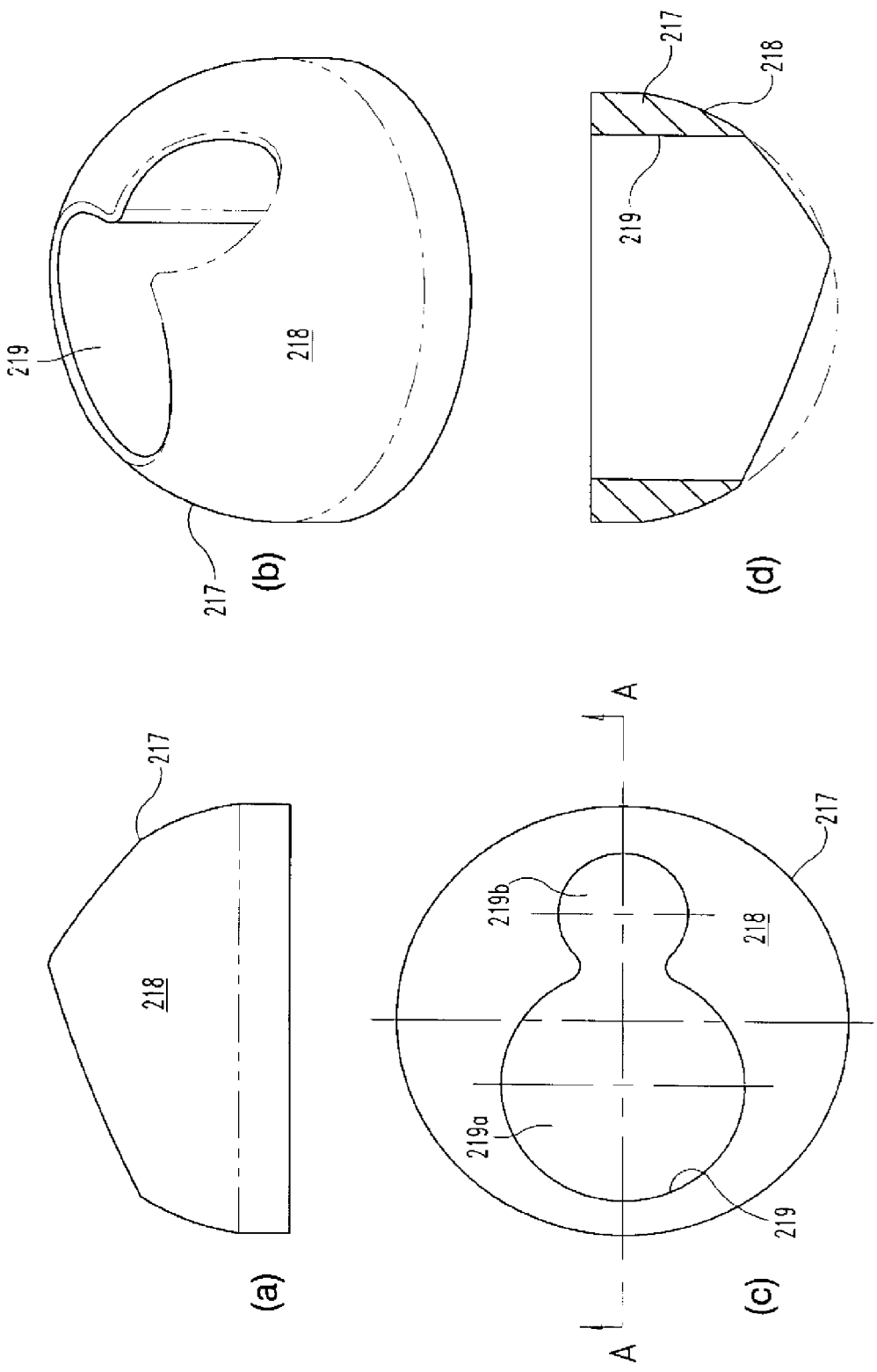
FIGS. 11(a)-11(d) are side, perspective, top and cross-sectional views of a stop mounted to the injection needle of the assembly of FIGS. 9-10.

As shown in the detail views of FIGS. 11(*a*)-(*d*), the stop 217 includes a contoured surface 218 which is preferably defined at a spherical radius. This contoured surface engages the seal, as described herein. The stop further defines an opening or bore 219 therethrough that is configured to conform to the outer surface geometry of the injection needle 210. Thus, the bore 219 includes a larger portion 219*a* that is sized to snugly receive the primary cannula 212 and a smaller portion 219*b* that is sized to snugly receive the secondary vent cannula 214. The stop 217 is connected to the injection needle 210 in a manner so that the stop cannot slip along the needle when the seal 220 is pressed between the stop and the disc annulus. Moreover, it is preferable that the stop be connected to the needle in a fluid-tight manner so that no fluid (or no appreciable amount of fluid) may leak between the stop and needle. Thus, in a preferred embodiment the stop 217 is affixed in a conventional manner, such as by welding or bonding. Other forms of connection are contemplated provided that the stop cannot slip proximally along the needle and provided that a fluid-tight connection is ensured.

Figure 12:
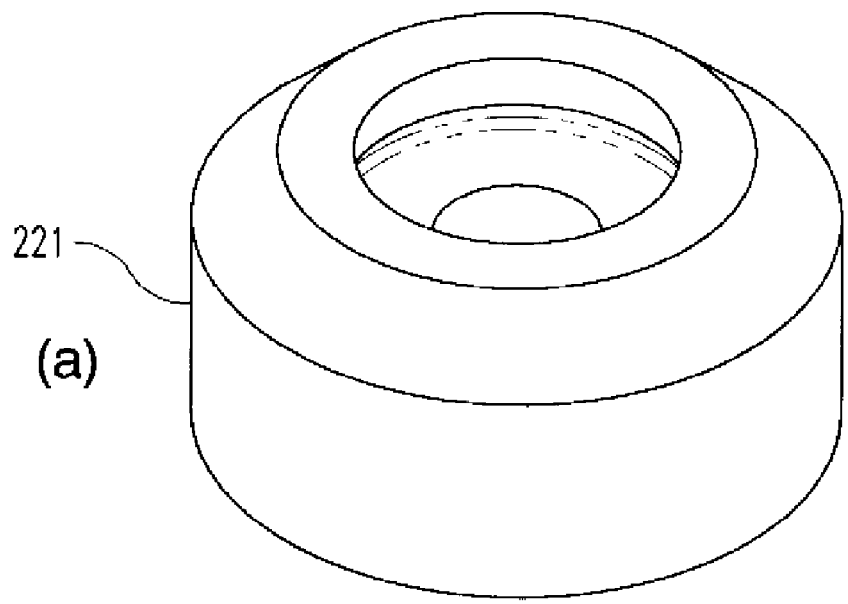
FIGS. 12(a)-12(b) are perspective and cross-sectional views of a cylindrical seal for use with the needle assembly shown in FIG. 9.
Figure 12:
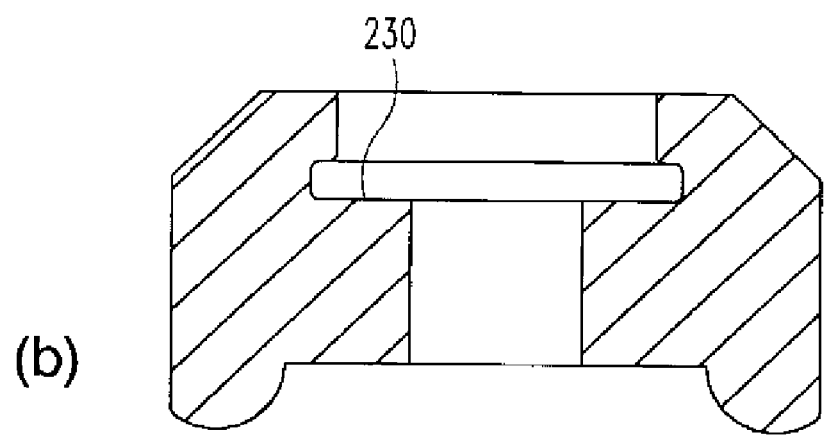
Figure 13:
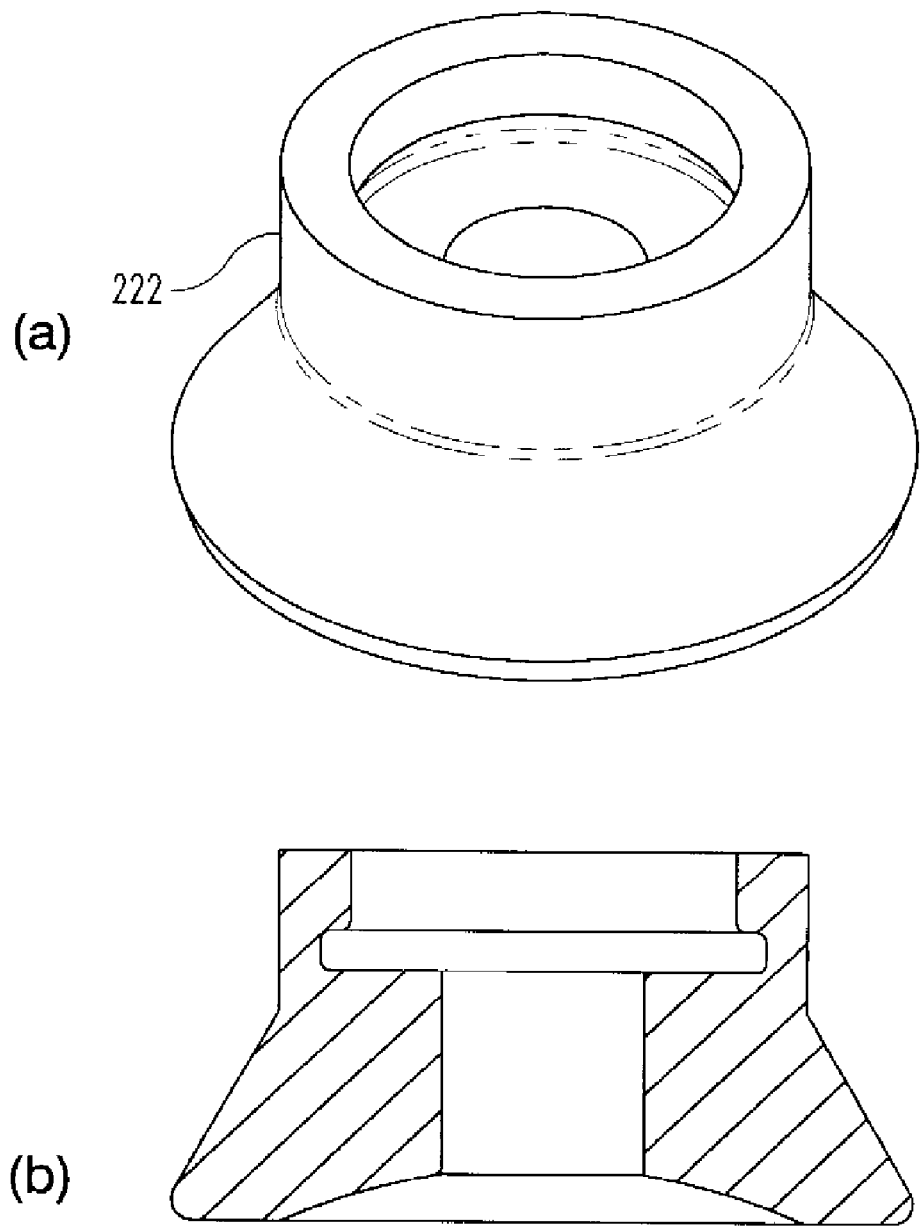
FIGS. 13(a)-13(b) are perspective and cross-sectional views of a cup-shaped seal for use with the needle assembly shown in FIG. 9.
Figure 14:
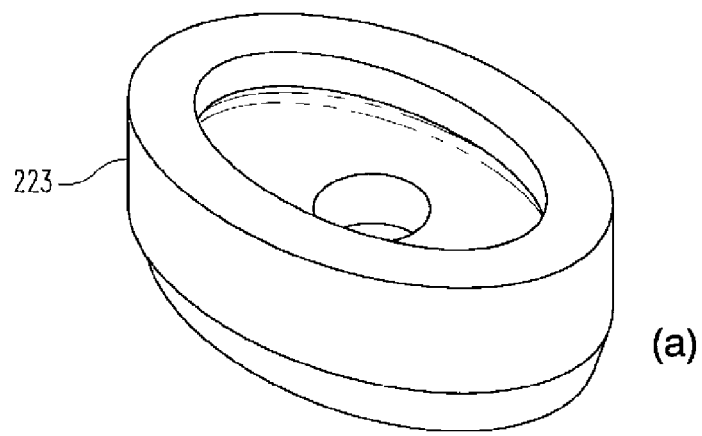
FIGS. 14(a)-14(c) are perspective, top and cross-sectional views of an elliptical seal for use with the needle assembly shown in FIG. 9.
Figure 14:
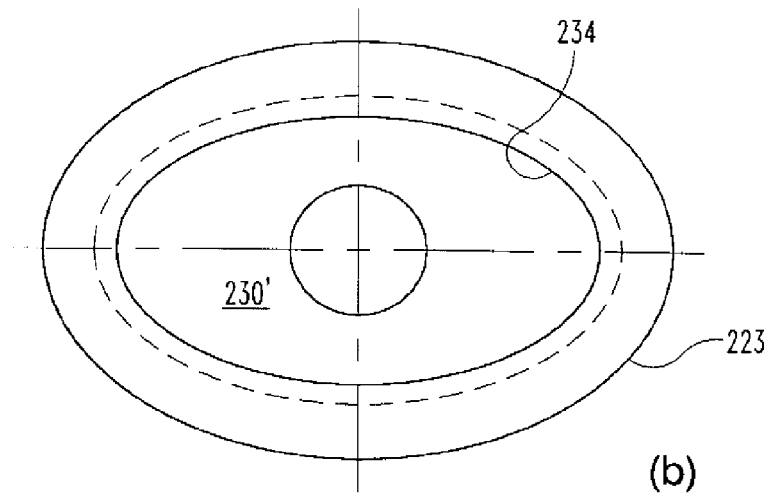
Figure 14:
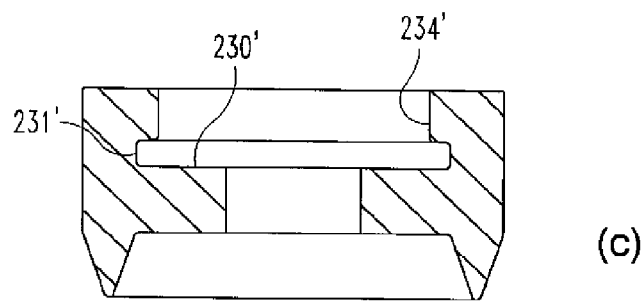

Returning to FIGS. 9(*a*)-(*f*), various seal configurations are shown for use in the needle assembly 200. The configuration of the seals may vary to accommodate different surgical procedures and different disc anatomies. For example, three seals 221, 222 and 223 in FIGS. 9(*a*), 9(*b*) and 9(*c*), respectively, including corresponding sealing surfaces 221*a*, 222*a* and 223*a* that are optimally configured for use in AMD procedures. As explained above, in a typical AMD procedure, the disc access is obtained through an existing tear or rupture in the disc annulus. In this case, the irregularity of the opening in the annulus requires a greater coverage area for the seal. Thus, the sealing surface 221a of the seal 221 provides a circular coverage area at a relatively large diameter, about 9.5 mm in the illustrated embodiment, as shown in the detail views of FIGS. 12(a)-(b). Likewise, the cup-shaped sealing surface 222a of the seal 222 may be provided in the same diameter, as shown in FIGS. 13(a)-(b). For cases in which the opening in the annulus is in the nature of a tear, an elliptical sealing surface 223a of the seal 223 in FIGS. 14(a)-(c), may be provided. The elliptical shape of sealing surface 223a also allows for greater potential angulation of the injection needle 210 while still sealably covering an irregular opening in the annulus.

As described above, the typical DDD procedure involves providing a prepared access opening through the annulus. Thus, the opening may be more readily controlled and sized to receive the injection needle 210. In certain cases, the controlled opening may have a diameter of about 2.5 mm, or less than about 5.0 mm. This controlled access opening size permits the use of a smaller seal, such as the circular seal 225 shown in FIGS. 16-18. This seal may have an outer diameter of about 6.5 mm. Alternatively, since the prepared opening in the annulus in a DDD may be made circular (as opposed to the irregular openings encountered in an AMD), the seal may be conical, like the seals 226 and 227 of FIGS. 9(e)-(f). As shown in the detail view of FIGS. 19(a)-(b), the sealing surfaces 226a, 227a and 228a of these seals may taper from a diameter of 3 mm to a diameter of 6.5 mm. The taper may be at a 30° or a 45° angle, for example, with commensurate adjustments in the overall length of the seal.

In certain embodiments, the interface between any of the seals 220-227 and the stop 217 may be fixed—i.e., the seal is pressed onto the needle 212 and against the stop 217 in a manner that does not permit any relative angulation or articulation. In these embodiments, the surface 218 of the stop 217 may be generally flat to bear against an interior surface of the seal, such as surface 230 of the seal 221 shown in FIG. 12(b). However, it is preferable that the interface between the seal and the needle accommodate some articulation since some manipulation of the injection needle within the disc may be desirable. For instance, movement of the distal end 211 of the needle 210 may be desirable to direct the fluent material, or injectable nucleus material, throughout the disc space. In this case it is important that the seal 220 maintain fluid-tight contact with the disc annulus.

Figure 18:
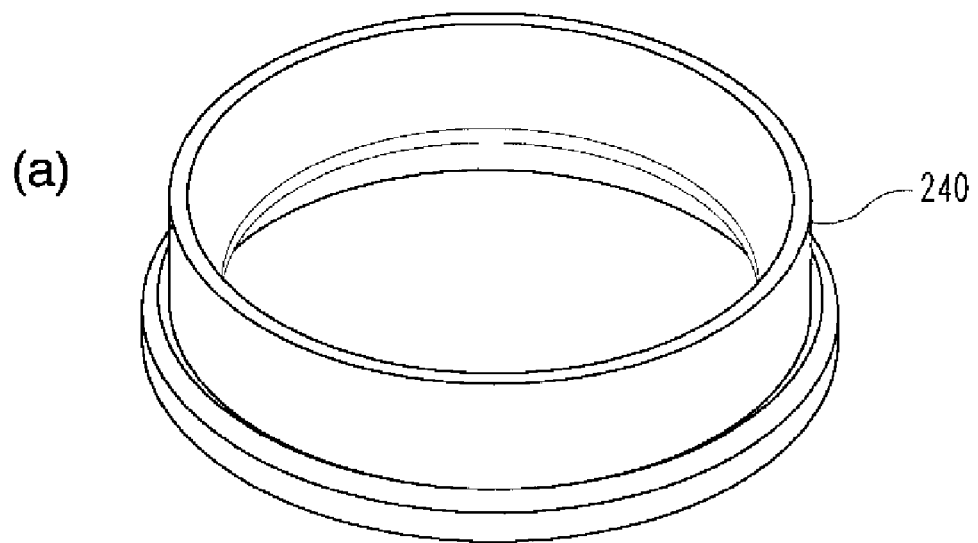
FIGS. 18(a)-18(b) are perspective and cross-sectional views of a bearing member for use with the cylindrical seal shown in FIG. 17.
Figure 18:
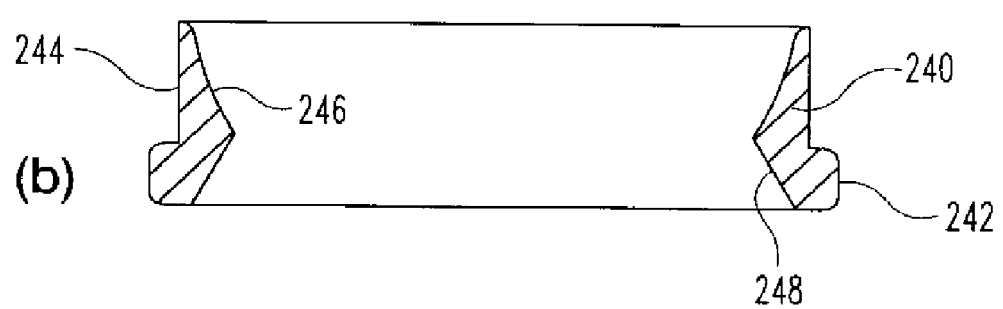

Thus, in certain embodiments a bearing element 240, as shown in FIGS. 16(b) and 18, may be disposed in the body of the selected seal in which the bearing element includes a complementary contoured surface 246 adapted for articulating contact with the surface 218 of the stop 217 (FIG. 11). Thus, for the spherical contoured surface 218, the complementary contoured surface 246 of the bearing element is preferable a spherical convex surface, as illustrated in FIG. 18. The bearing element 240 includes a circumferential flange 242 and a cylindrical portion 244 in which the convex surface is defined. A tapered exit surface 248 is defined in the flange 242, as shown in FIG. 18(b), to provide clearance for the needle 210 as it moves through a spherical angle. In the illustrated embodiment, the exit surface may be tapered at a 60° spherical radius.

Figure 17:
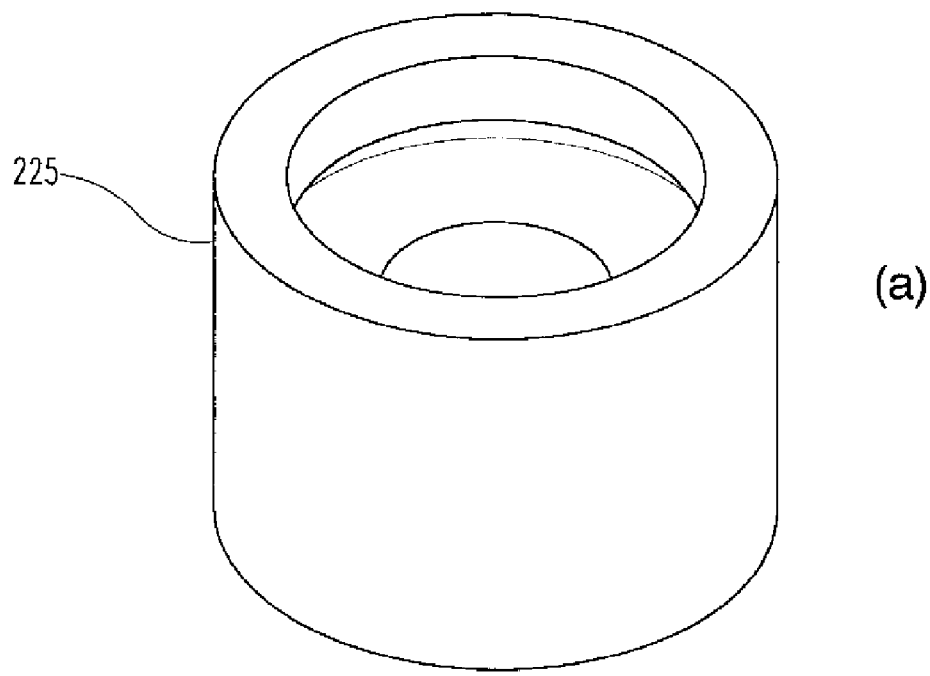
FIGS. 17(a)-17(b) are perspective and cross-sectional views of the seal body of the cylindrical seal shown in FIG. 16.
Figure 17:
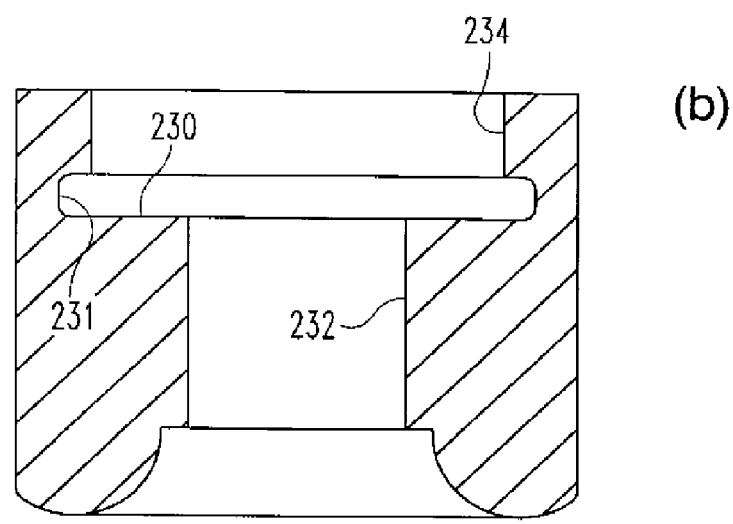

The body of the seal, such as seal 225 shown in FIGS. 9(d) and 17, is configured to receive the flange 242. Thus, in the illustrated embodiment, the seal defines an internal groove 231 at the mating surface 230. The internal groove is sized to receive the flange 242 in fluid-tight engagement. Similarly, the seal 225 defines a cylindrical bore 234 for fluid-tight engagement around the cylindrical portion 244 of the bearing element 240. The central bore 232 extends through the seal to receive the needle 210, as described above.

Figure 15:
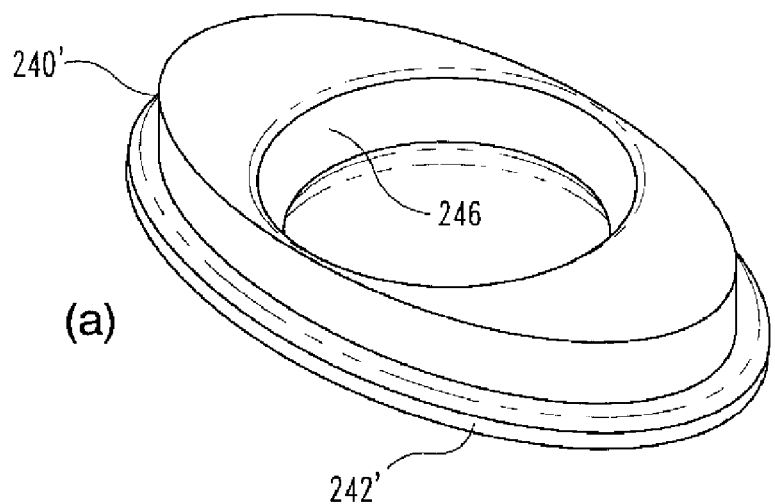
FIGS. 15(a)-15(b) are perspective and cross-sectional views of a bearing member for use with the elliptical seal shown in FIG. 14.
Figure 15:
Figure 16:
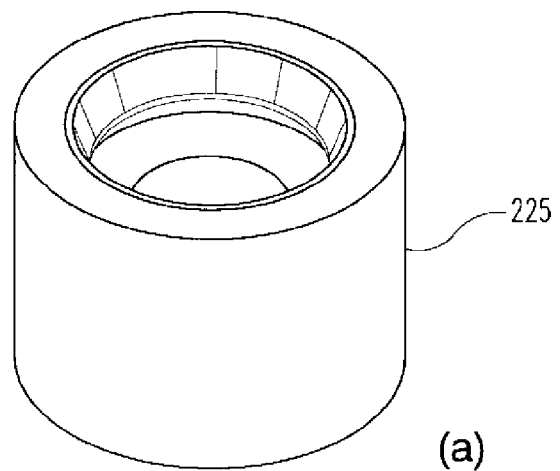
FIGS. 16(a)-16(b) are perspective and exploded views of another cylindrical seal for use with the needle assembly shown in FIG. 9.
Figure 16:
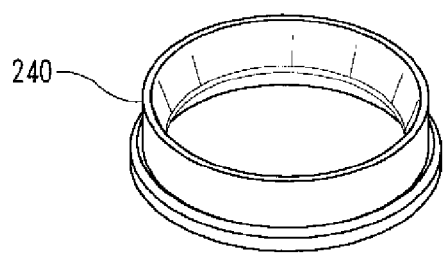
Figure 16:
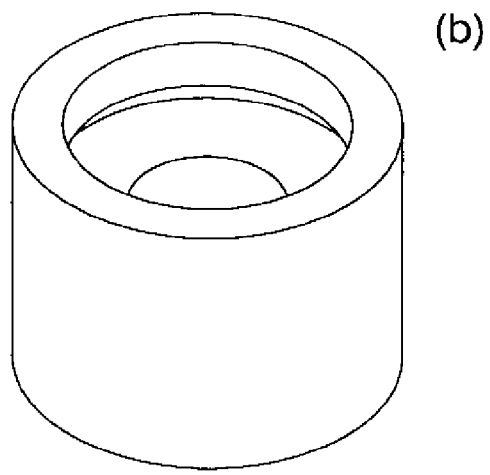

The body of the seals 221-227 may be similarly configured to receive a corresponding bearing element 240. The elliptical seal 223 may incorporate a modified bearing element 240', as shown in FIG. 15, to interface with the elliptical interior features 230', 231' and 234' of the seal 223 illustrated in FIG. 14. However, the bearing element 240' includes the same spherical convex interior surface 246 for articulating engagement with the surface 218 of the stop 217.

Since the seals 221-227 are intended for fluid-tight engagement to the disc annulus the seals are preferably formed of a resilient conformable or compliant biocompatible material. Most particularly for the seals 221, 222, 223 and 225, the seal material must be compliant enough to conform to the surface of the annulus under manual pressure. Thus, in one embodiment, the seals are formed of a resilient polymer, such as silicone. In one specific embodiment, the seal is formed of Dow Corning MDX4-4210 silicone. It can be appreciated that the conical seals 226 and 227 may also be formed of the same compliant and resilient material; however, since the body of the conical seals is intended to be engaged within the opening in the annulus the need for the seal to conform to the annulus is less critical. Thus, or the conical seals 226 and 227, the body of the seal may be formed of a more rigid biocompatible material, such as a high density plastic or resin, or a meta such as stainless steel.

Since the stop 217 and bearing element 240 are intended to articulate in bearing contact, these components are preferably formed of a bearing material, such as 304 stainless steel. Alternatively, these elements may be formed of a high density plastic or resin suitable or bearing contact, such as DELRIN® acetal resin.

In accordance with one aspect of the invention, a kit of modular needle components may be provided. In particular, several needles 210 having different stop locations may be provided in the kit. Likewise, a selection of seals may be provided in the kit, including the seals 221-227 and variations thereof. The kit allows the surgeon to defer the selection of the injection needle assembly until the nature of the injectable nucleus injection procedure is ascertained. In other words, the surgeon may determine whether an AMD or a DDD procedure is indicated and evaluate the disc anatomy to determine what combination of needle and seal is appropriate. Once the selection is made, the seal 220 is easily slid onto the distal end 211 of the needle 210 until the seal contacts the stop 217. In use, the surgeon may maintain manual pressure on the needle assembly 200 to press the seal against the disc annulus.

Figure 20:
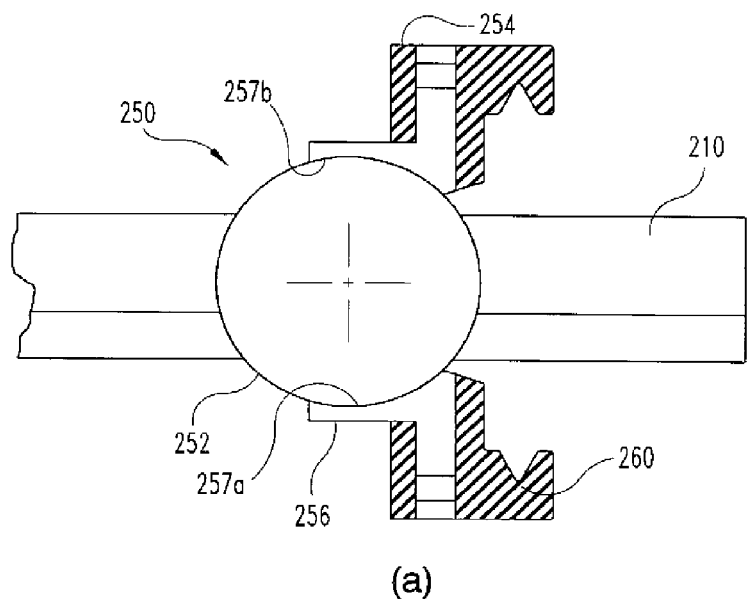
FIG. 20(a) is a side partial cross-sectional view of an alternative articulating seal assembly with the needle assembly shown in FIG. 9.
FIG. 20(b) is a top view of the articulating seal shown in FIG. 20(a).
FIG. 20(c) is an end view of the needle in the assembly of FIG. 20(a).
FIG. 20(d) is an end view of the assembly shown in FIG. 20(a).
Figure 20:
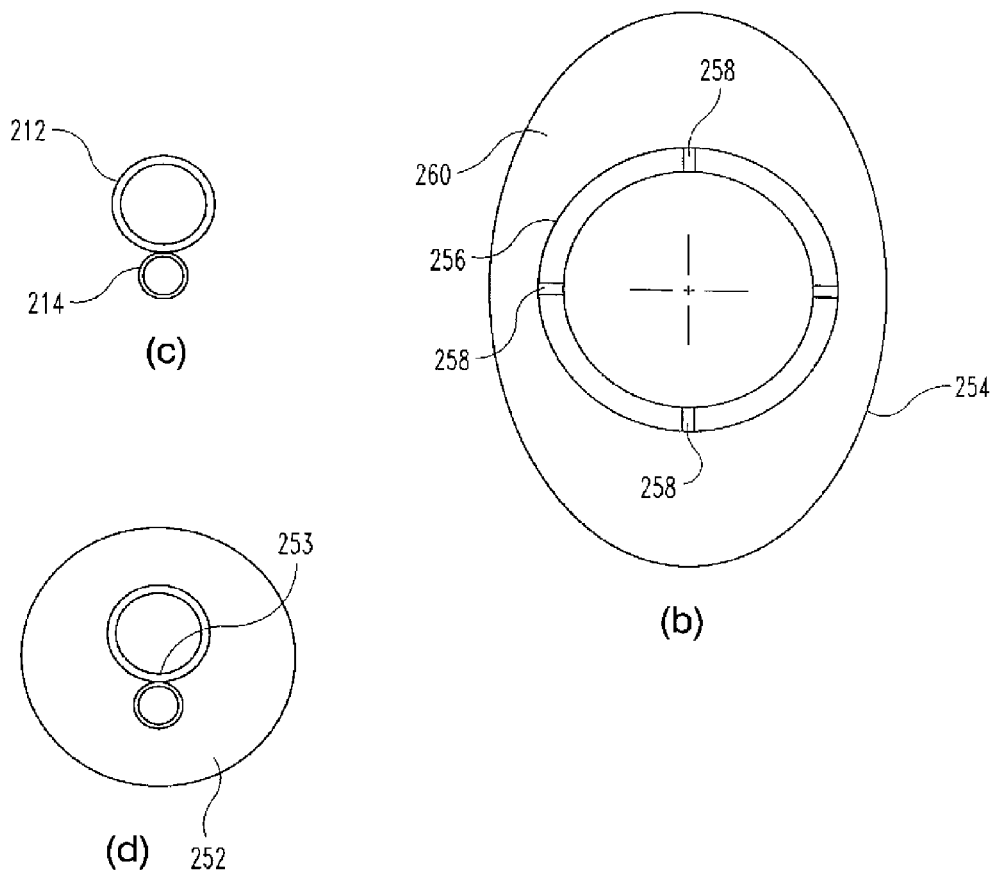
Figure 21:
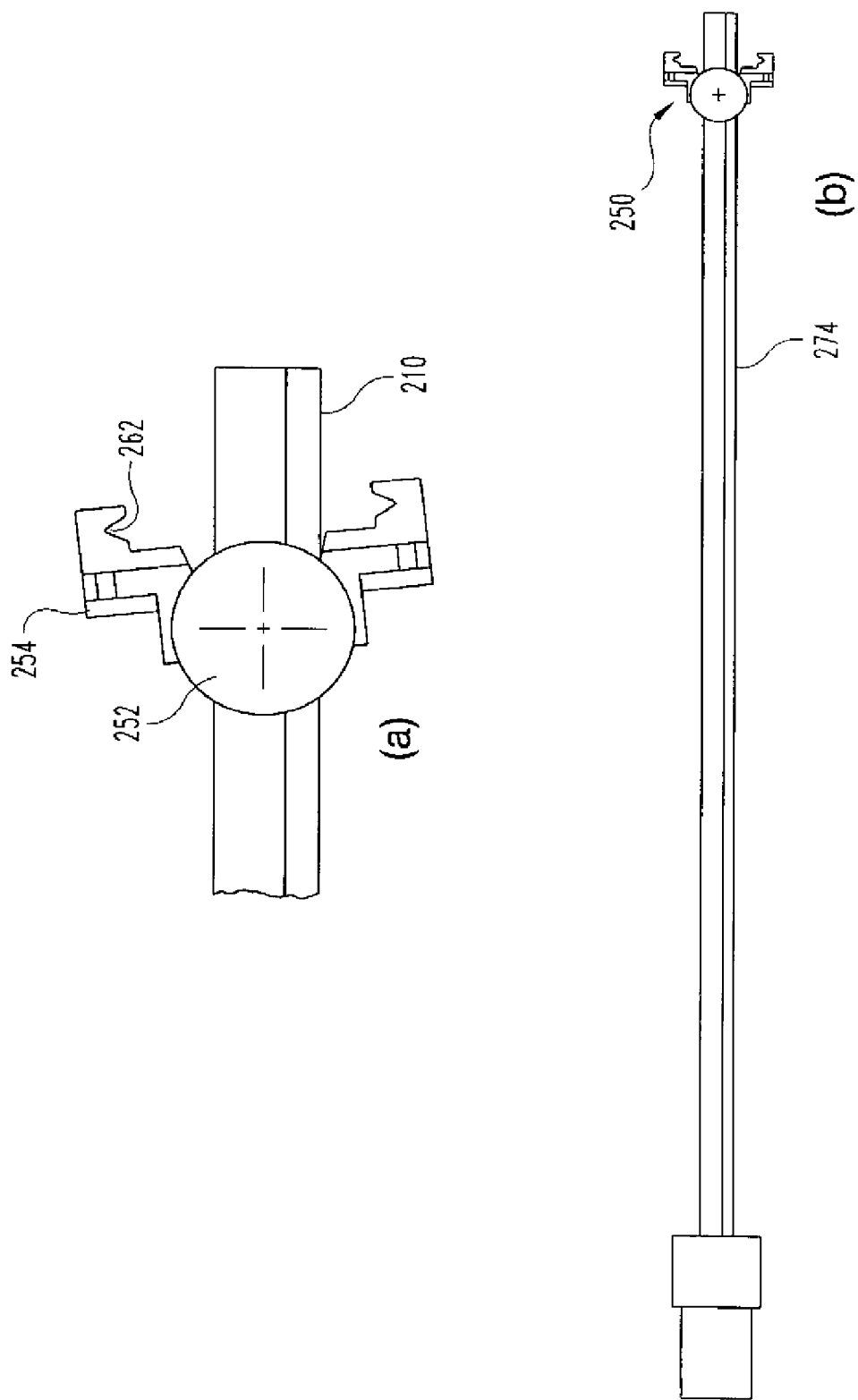
FIG. 21(a) is a side view of the articulating seal assembly shown in FIG. 20(a) with the seal oriented at an angle relative to the needle.
FIG. 21(b) is a side view of the articulating needle assembly shown in FIG. 20.

Referring to FIGS. 20-21, an articulating modular seal 250 is provided that permits a wider range of angulation between the seal and the cannula. The seal assembly 250 includes a substantially spherical ball 252 that is affixed to the injection needle 210 that operates as the stop. In one embodiment, the ball 252 is formed of a bearing material, such as 304 stainless steel, and is suitably affixed in sealed engagement to the injection cannula 212 and the vent cannula 214. The ball may define bores 253 through which the injection needle 210 is inserted and welded in position. It is understood that the ball 252 operates as a stop, similar to the stop 220 affixed to the injection needle shown in FIGS. 9-10 as described above.

In this embodiment, the modular seal 250 incorporates a snap-fit or press-fit engagement between the seal and the ball/stop. Thus, the modular seal may include a seal 254 that incorporates a cap or collar 256 configured to be fixed in bearing contact with the ball 252. The cap 256 may thus include a spherical cavity 257a that terminates in an upper lip 257b. The cavity and lip are configured to capture the ball therein in a snap-fit or press-fit engagement. Thus, the lip 257b is configured so that over half of the ball 256 is captured within the spherical cavity 257a. The cap 256 may be provided with slits 258 that separate as the ball is pressed past the lip 257b into the cavity 257a.

Figure 9:
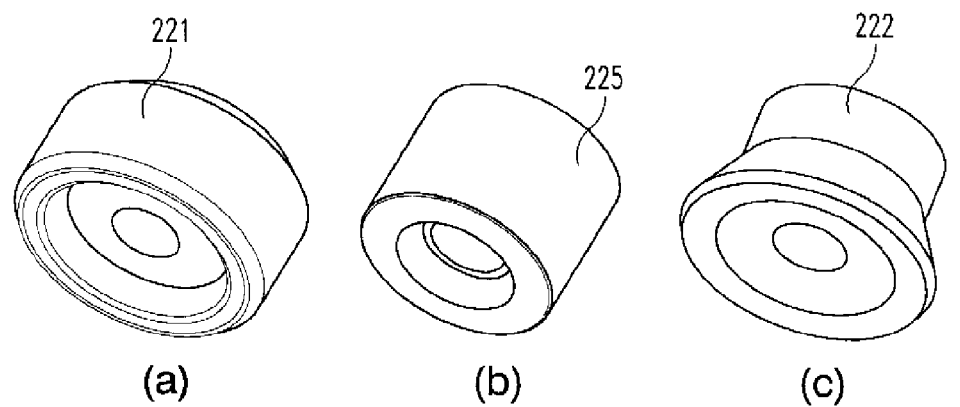
FIGS. 9(a)-9(g) are perspective views of an injection needle assembly with a modular seal in accordance with the present invention, and of several modular seals for use with the needle assembly.
Figure 9:
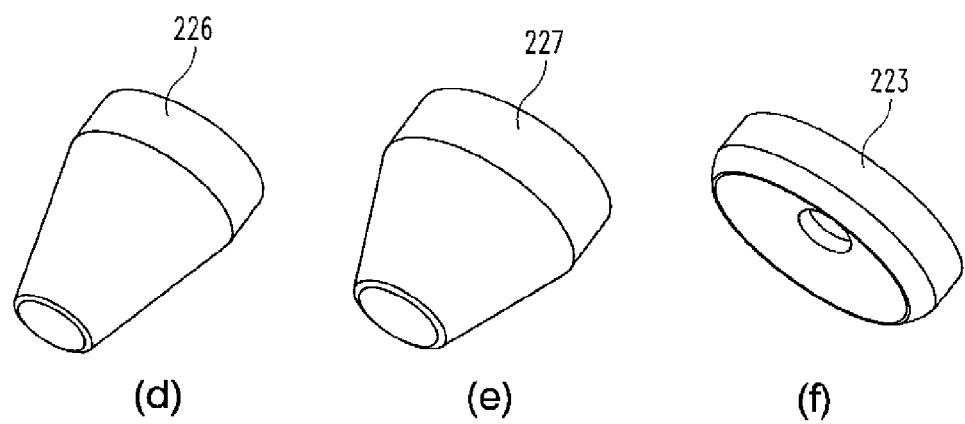
Figure 9:
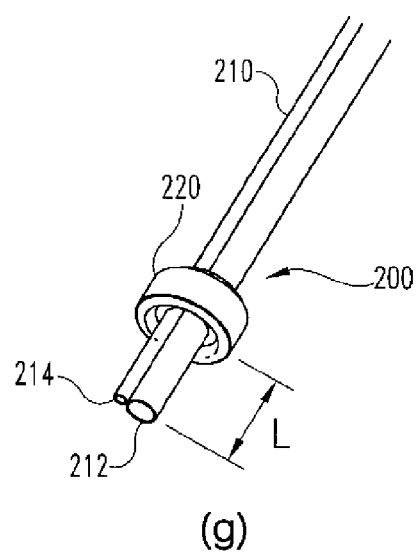
Figure 10:
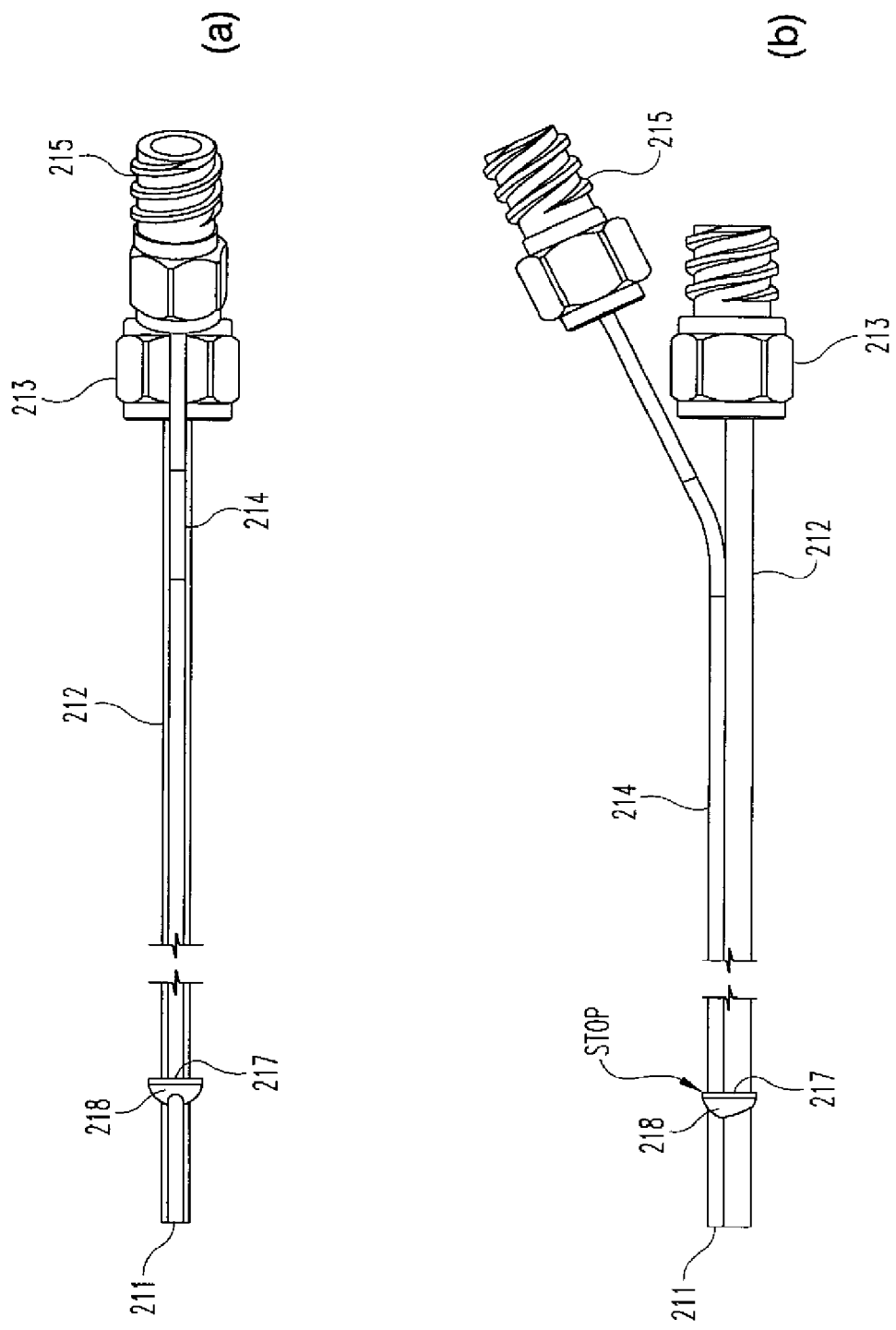
FIGS. 10(a)-10(b) are side and top views of the injection needle assembly shown in FIG. 9(g).

The seal 254 further includes a seal body 260 that may be configured like any of the seals 221-225 illustrated in FIG. 9. The body 260 preferably defines a cavity 262 as shown in FIG. 21(a) that is positioned over the opening in the disc annulus. The cavity further includes an angled wall 264 that provides clearance for the injection needle 210 as the seal and needle are pivoted relative to each other. Thus, in one specific embodiment, the injection needles 210 may be manipulated through a 20° spherical angle as the injectable nucleus material is introduced through the cannula 212. Of course, as with the prior embodiments, the modularity of the modular seal 250 contemplates a selection of seals 254 and a selection of injection needles 210 with different positions for the ball stop 252, as described above.

Figure 22:
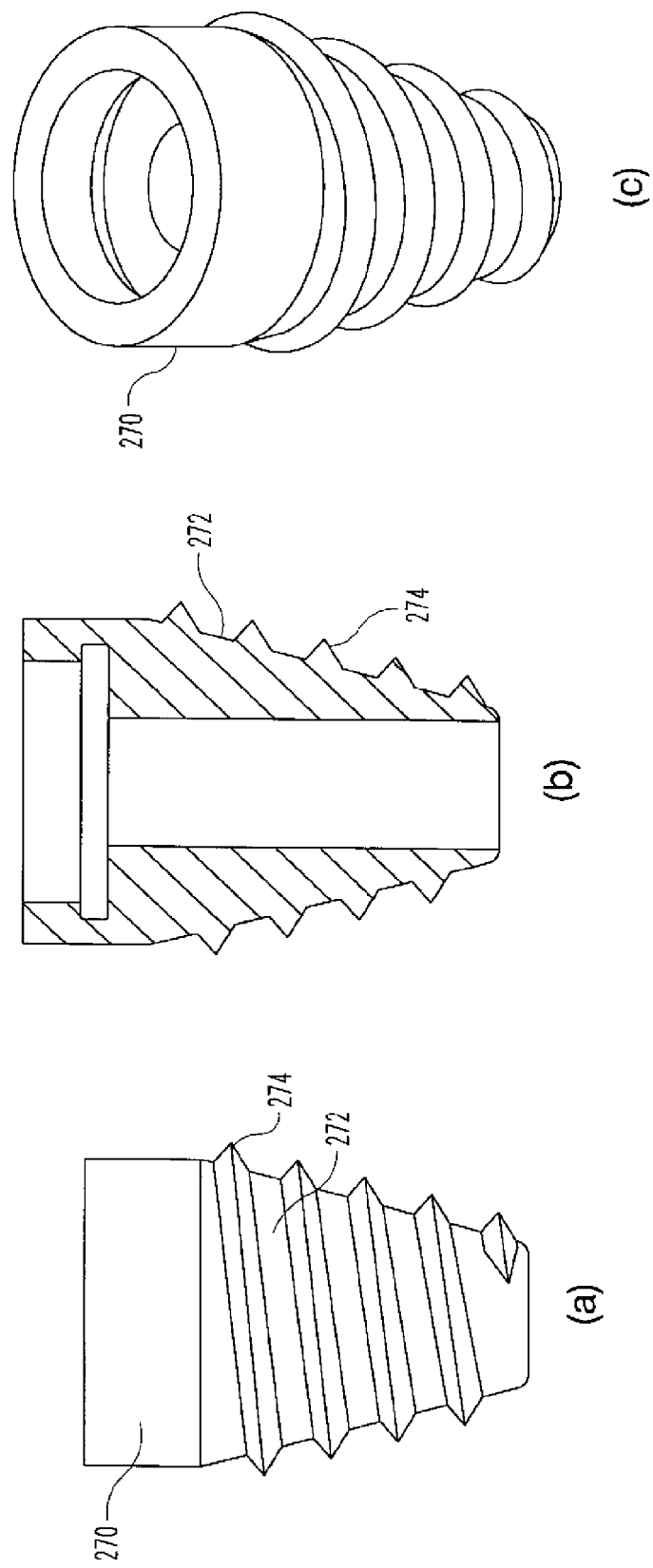
FIGS. 22(a)-22(c) are side, cross-sectional and perspective views of a self-anchoring seal for use with the needle assembly shown in FIG. 9.

In an alternative embodiment, the seal may incorporate self-anchoring features—i.e., features that temporarily anchor the seal to the disc annulus in a fluid-tight connection. One such seal is the seal 270 shown in FIG. 22. This seal may be a modification of the seal 226 or 227 shown in FIGS. 9 and 19. In particular, the seal 270 includes a conical body 272 that is adapted to be pressed into the prepared opening through the disc annulus, as might arise in an AMD procedure. Threads 274 are provided on the conical body for threaded engagement within the annulus to anchor the seal as well as the injection needle to the disc. In practice, the needle, with the seal mounted thereon, is introduced through the opening in the annulus until the threads of the seal contact the opening. The seal 270 may then be manually rotated to engage the opening and advance the seal farther into the annulus.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A needle assembly for use in sealably injecting a biomaterial into an intradiscal space accessed through an opening in an annulus of a spinal disc, comprising: a needle sized for introduction through the opening in the annulus, said needle having a passageway for injecting the biomaterial therethrough, a proximal end adapted to engage a source of the biomaterial and a distal end configured to be disposed within the intradiscal space when said needle extends through the opening in the annulus; a stop affixed directly to said needle at a pre-determined distance from said distal end in a manner such that said stop cannot slip along said needle, said pre-determined distance defining a location of said distal end within the intradiscal space when said needle extends through the opening in the annulus; and a seal disposed on said needle and bearing in a fixed interface against said stop between said stop and said distal end, said seal sized and configured to not pass through said opening and including a sealing face configured to sealingly engage the annulus around said needle when said needle extends through the opening in the annulus, wherein said sealing face defines an area of contact with an outer surface of the annulus, said stop providing a pressure surface to press said sealing face between said outer surface of the annulus and said stop upon application of manual pressure thereto.

2. The needle assembly of claim 1, wherein said seal is slidably disposed on said needle.

3. The needle assembly of claim 1, wherein said area of contact is circular.

4. The needle assembly of claim 1, wherein said area of contact is elliptical.

5. The needle assembly of claim 1, wherein said seal includes:
   a seal body including said sealing face; and
   a bearing element attached to said seal body, said bearing element including a bearing surface bearing against said stop.

6. The needle assembly of claim 5, wherein said seal body and said bearing element are formed of different materials.

7. The needle assembly of claim 1, wherein said stop is affixed to said needle in a fluid-tight manner.

8. The needle assembly of claim 1, wherein said stop is affixed to said needle selected from the group of connections consisting of welding and bonding.

\* \* \* \* \*